(12) United States Patent
Niemann et al.

(10) Patent No.: US 10,444,058 B2
(45) Date of Patent: Oct. 15, 2019

(54) DEVICE FOR MEASURING A FILL LEVEL OF A LIQUID IN A CONTAINER WITH AN ULTRASONIC SENSOR

(71) Applicant: Hella KGaA Hueck & Co., Lippstadt (DE)

(72) Inventors: Thomas Niemann, Delmenhorst (DE); Jürgen Palloks, Westerstede (DE)

(73) Assignee: HELLA KGAA HUECK & CO., Lippstadt (DE)

( * ) Notice: Subject to any disclaimer, the term of this patent is extended or adjusted under 35 U.S.C. 154(b) by 115 days.

(21) Appl. No.: 15/715,910

(22) Filed: Sep. 26, 2017

(65) Prior Publication Data

US 2018/0087950 A1 Mar. 29, 2018

(30) Foreign Application Priority Data

Sep. 27, 2016 (DE) ........................ 10 2016 118 225

(51) Int. Cl.
| | | |
|---|---|---|
| *G01F 23/296* | (2006.01) | |
| *G01N 29/22* | (2006.01) | |
| *G10K 11/00* | (2006.01) | |
| *G01H 3/00* | (2006.01) | |

(52) U.S. Cl.
CPC ...... *G01F 23/2962* (2013.01); *G01F 23/2968* (2013.01); *G01N 29/221* (2013.01); *G01N 29/223* (2013.01); *G10K 11/004* (2013.01); *G01H 3/00* (2013.01)

(58) Field of Classification Search
CPC . G01F 23/2962; G01N 29/223; G01N 29/221

USPC .......................................................... 73/632
See application file for complete search history.

(56) References Cited

U.S. PATENT DOCUMENTS

| | | | | |
|---|---|---|---|---|
| 6,629,457 B1 * | 10/2003 | Keller | ................... | F02D 33/003 367/908 |
| 7,213,456 B2 * | 5/2007 | Rollwage | ............ | G01F 23/2962 181/124 |
| 8,180,582 B2 * | 5/2012 | Knowles | ............. | G01F 23/2962 324/691 |
| 8,302,472 B2 * | 11/2012 | Rumpf | ................... | B60K 15/00 73/290 V |
| 10,197,431 B2 * | 2/2019 | Fedgenhaeuer | ........ | F01M 11/12 |

(Continued)

FOREIGN PATENT DOCUMENTS

| | | |
|---|---|---|
| DE | 102007014540 A1 | 10/2008 |
| DE | 102014009543 A1 | 12/2015 |

*Primary Examiner* — Jacques M Saint Surin
(74) *Attorney, Agent, or Firm* — Muncy, Geissler, Olds & Lowe, P.C.

(57) ABSTRACT

In a device for measuring a fill level of a liquid in a container with an ultrasonic sensor which is arranged on a floor element, wherein a damping cup with a measuring tube is assigned to the ultrasonic sensor, the damping cup has an external housing and an internal housing. The internal housing contains the measuring tube, and either the internal housing has outwardly protruding contact elements that lie against the inside of the external housing or the external housing has outwardly protruding contact elements that lie against the outside of the internal housing. The external housing is also provided and designed for pluggable mounting of of the internal housing, and a channel is formed between the internal housing and the external housing.

11 Claims, 1 Drawing Sheet

(56) References Cited

U.S. PATENT DOCUMENTS

| | | | | |
|---|---|---|---|---|
| 2011/0226212 A1* | 9/2011 | Niemann | ............... | F01M 11/12 |
| | | | | 123/196 R |
| 2013/0160433 A1* | 6/2013 | Schepers | ............. | G01F 23/2963 |
| | | | | 60/295 |
| 2015/0292382 A1* | 10/2015 | Maguin | ................ | F01N 3/2066 |
| | | | | 60/295 |

* cited by examiner

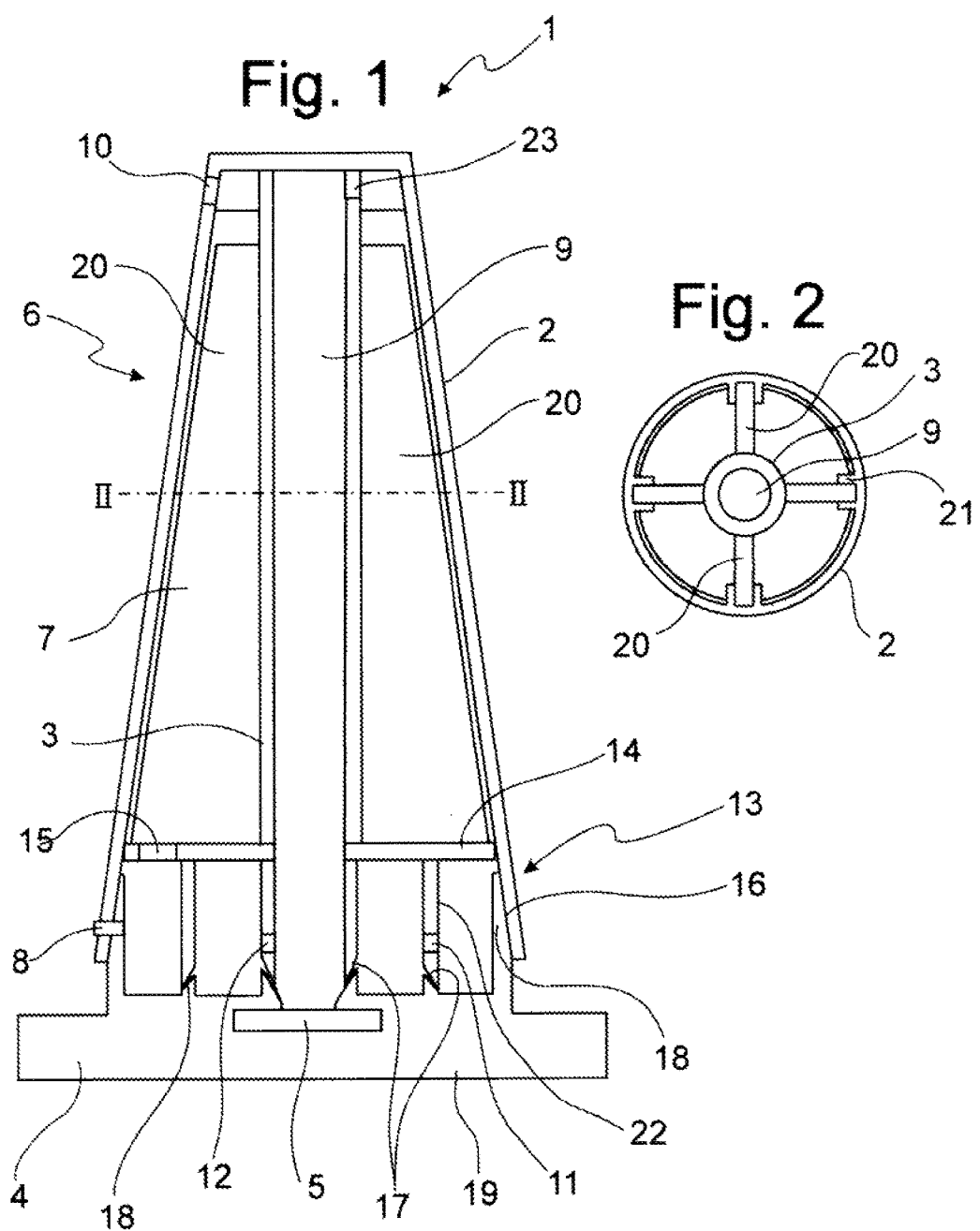

DEVICE FOR MEASURING A FILL LEVEL OF A LIQUID IN A CONTAINER WITH AN ULTRASONIC SENSOR

The invention relates to a device for measuring a fill level of a liquid in a container with an ultrasonic sensor which is arranged on a bottom element, wherein a damping cup with a measuring tube is assigned to the ultrasonic sensor.

A species-related device for measuring a fill level of a liquid is known for example from DE 10 2014 009 543 A1. That device is more particularly a container for holding engine oil. These are needed particularly in motor vehicles. In order to determine the oil level in the container, ultrasonic waves are emitted from the bottom of the device and reflected by the boundary surface between the oil and the air above it, and are received by the ultrasonic sensor again. The fill level in the container can then be determined from the detected travel time of the ultrasonic waves. However, in an engine which is running, particularly in a motor vehicle, it is difficult if not impossible to determine the oil fill level, because the oil is heavily foamed and the sonic waves are reflected by gas bubbles. The values detected therefore differ widely. In order to be able to take a measurement with readable values, an unambiguous boundary surface between the gas and oil media is required. To achieve this, devices called damping cups are attached to the ultrasonic sensors. Inside these damping cups, which enclose the measuring section of the ultrasonic sensor, the liquid that is to be measured is calmed, and communicates with the container only through a small opening in the damping cup. Relatively few gas bubbles get into the damping cup through the small opening between the damping cup and the container. The fill level in the damping cup is equal to the fill level outside the damping cup, but at the same time fluctuations that are caused for example by acceleration or cornering are slowed. Typically, an antechamber is also assigned to the damping cup and serves to degas the liquid to be measured, particularly foamed oil, thus creating a liquid inside the measuring section of the damping cups that has been degassed and is relatively bubble-free. The damping cups are typically made of plastic, usually from several parts that have been welded, clipped or bonded together.

The object underlying the invention is to create a device of the kind described in the introduction which is of simple construction and particularly easy to install.

This problem is solved with a device having the features of claim 1. Advantageous variants of the invention are described in the subordinate claims.

In a device for measuring a fill level of a liquid in a container with an ultrasonic sensor which is arranged on a floor element, wherein a damping cup with a measuring tube is assigned to the ultrasonic sensor, it is provided as essential to the invention that the damping cup has an external housing and an internal housing, that the internal housing includes the measuring tube, either that the internal housing has outwardly protruding contact elements which lie against the inside of the external housing, or that the external housing has inwardly protruding contact elements which lie against the outside of the internal housing, that the external housing is provided and designed for the pluggable mounting of the internal housing, and that a channel is formed between the internal housing and the external housing, and the the lower end regions of the internal housing and the external housing are connected to the floor element. With such a device, it is particularly easy to mount the damping cup. The damping cup consists of only two parts, the internal housing and the external housing. It is only necessary to plug these two parts into each other. The entire device consists of just three assemblies, the damping cup in two parts and the floor element, which also includes the ultrasonic sensor. The internal housing and the external housing are about the same length and their lengths differ preferably by less than 20%, particularly by less than 10%, more particularly by less than 5%. In the attached state, the internal housing downwards slightly beyond the external housing, but preferably by less than 10%, more preferably by less than 5% of the height of the external housing. The damping cup is welded to the floor element.

In a preferred variant of the invention, the lower region of the internal housing has an antechamber. The internal housing is a single-part element. It is preferably a plastic element, particularly a plastic injection moulded part. The antechamber has an inlet opening with one or more rings, through which the liquid, particularly the oil must pass, undergo degassing and then enter the measuring tube through an aperture. A projecting edge is arranged on the internal housing above the antechamber, and in the plugged state this lies flush against corresponding matching surfaces on the external housing to function as a seal, thus closing the antechamber off at the top. The projecting edge is also interrupted in one area leaving a channel free through which oil foam that enters can pass through upwards into the channel between the internal housing and the external housing and flow out in a ventilation opening in the external housing.

The external housing is preferably also a single-part element. It is preferably made of plastic and is preferably a plastic injection moulded part.

In another variant of the invention, a ventilation aperture is provided in the upper region of the external housing. This opens the top of the channel between the internal housing and the external housing so that oil foam entering at the bottom can escape there directly. This ventilation aperture of the external housing also communicates directly with an upper ventilation aperture in the measuring tube, so that pressure can be balanced via the ventilation aperture in the external housing. The ventilation aperture in the measuring tube and the ventilation aperture in the external housing are preferably arranged with an offset relative to each other, particularly by 180°, so that any oil foam entering through the ventilation aperture in the external housing is prevented from then also passing directly into the ventilation aperture in the measuring tube.

In a particularly preferred refinement of the invention, in the plugged state the internal housing protrudes downwards beyond the external housing. This makes it easier to assemble the internal housing by plugging it into the external housing, and also simplifies aligning and connecting the bottom edges of the external and internal housings with the floor element. The lower regions of the internal and external housings are preferably welded to the floor element. For this purpose, the bottom end regions of the internal housing and external housings and/or the corresponding mating surfaces on the floor element are sloping. The bearing surfaces are enlarged thereby, yielding a larger contact area on which a welded connection can be created more easily and more reliably. Alignment is also made easier, because the surfaces which bear on each other at an angle are self-aligning to some degree. At the same time, the lower end region of the external housing is preferably inclined more steeply than the lower end region of the internal housing. Since the external housing is also shorter overall than the internal housing and the corresponding outer wall of the flange in the outer region for contacting the external housing is higher than the contact regions for the internal housing, a first contact is created in the lower end region of the external housing with the long sloping elements and contact angles or inclination angles in the order of 10° to 20°. Not until afterwards is contact made between the internal housing and the assigned sloping elements, which have considerably steeper and shorter slopes than the sloping elements in the contact region of the external housing, in the order of 40° to 50°. This helps to ensure reliable, secure assembly.

The floor element is preferably constructed as a flange. Said flange can be mounted, particularly screwed into an oil sump or other receptacle from below. The ultrasonic sensor is mounted on the flange, and is directed upwards into the damping cup. In all, the device therefore consists of only three assemblies, that is to say the external housing, the internal housing and the flange.

In a preferred embodiment of the invention, the protruding contact areas extend over more than half the height of the damping cup. This creates a particularly secure, reliable connection between the internal housing and the external housing. Particularly preferably, said contact areas begin above the antechamber and adjoin it immediately. In a preferred variant of the invention, the protruding contact areas are constructed as vanes which are arranged on the internal housing and guided in correspondingly adapted grooves on the inside of the external housing. The protruding contact areas advantageously extend vertically, so that they are guided in the corresponding grooves during the plugging operation.

A free space which is unoccupied by the protruding contact areas is left in the upper region, thus allowing free access between the ventilation apertures of the internal housing and the external housing. Preferably, at least three protruding contact areas are present when viewed in cross section. In a preferred variant, four protruding contact areas are provided, offset by 90° relative to each other. If the contact areas are constructed continuously from the antechamber to the top, this forms a channel between the internal and external housings between two such protruding contact areas, that is to say in a preferred embodiment in about a quarter of the remaining space between the internal housing and the external housing.

A further aspect of the invention consists in the provision of an oil-lubricated engine, particularly an internal combustion engine equipped with a device as described in the preceding text. It is a further aspect of the invention that a motor vehicle is equipped with such an oil-lubricated engine having the oil level measurement device described above.

In the following, the invention will be explained further with reference to an exemplary embodiment represented in the drawing. In detail, the schematic diagrams show in:

FIG. 1: a cutaway side view of a device according to the invention; and

FIG. 2: a plan view along line II-II in FIG. 1.

FIG. 1 represents a cutaway side view of a device 1. Device 1 consists essentially of a damping cup 6 and a floor element 4, which in the present embodiment is embodied as flange 19. An ultrasonic sensor 5 is integrated in the floor element 4 or is arranged thereon. In this case, the floor element 4 is designed as a flange 19, which is also made evident by the fact that the flange 19 protrudes laterally beyond the structural surface of the damping cup 6 to form fastening areas there. A measuring tube 9, in which the actual measurement takes place, extends over the ultrasonic sensor 5. The ultrasonic sensor 5 emits ultrasonic waves, which propagate upwards inside the measuring tube 9, are reflected on a liquid/air phase boundary and are then received by the ultrasonic sensor 5 again as reflected ultrasonic waves. The distance from the ultrasonic sensor 5 to the phase boundary can then be calculated from the travel time of the ultrasonic waves, and from this the fill level may be calculated. The measuring tube 9 is a part of an internal housing 3. The internal housing 3 also constitutes an essential part of the lower region of the damping cup 6, in which an antechamber 13 ifs formed. The outermost wall of the antechamber 13 is constituted by an external housing 2. Otherwise, the antechamber 13 is formed by the wall of the measuring tube 9, a wall 22 in the internal housing 3, and an upper edge 14 of the internal housing 3. Said edge closes off the top of the antechamber 13. At the bottom, the antechamber 13 is closed by the floor element 4.

The antechamber 13 extends over about 20% to 25% of the height of the internal housing 3. The internal housing 3 is furnished with a plurality of protruding contact areas 20, of which two oppositely placed contact areas 20 are shown here. They begin at the measuring tube 9 of the internal housing 3 and extend as far as the inner wall of the external housing 2. This assures a firm seating for the internal housing 3 in the external housing 2. In particular, the external housing 2 has grooves corresponding to the protruding contact areas, which grooves are not shown here. Thus, the internal housing 32 can be pushed into the external housing 2 from below with positional reliability and assembled therein by plugging. A ventilation aperture 23 is provided on the upper edge area of the measuring tube 9, which aperture helps to balance the pressure as the liquid level rises. In the lower end region thereof, the walls 22 of the antechamber 13, which are part of the internal housing 3 are sloping and form inclined elements 17. The inclined elements of the measuring tube 9 are directed outwards, and the inclined elements of the walls 22 are directed inwards, that is to say in the opposite direction to the adjacent inclined elements 17 of the internal housing 3 in the region of the measuring tube 9. This results in a reliable self-centering arrangement on the corresponding inclined elements 18 of the floor element 4. The external housing 2 surrounds the internal housing 3, but is not constructed quite as wide or as long at the bottom, with the result that the internal housing 3 protrudes slightly beyond the bottom of the external housing 2. This makes assembly easier. An inlet opening 8 is provided in the bottom area of the external housing 2, through which the liquid, particularly oil enters through the wall of the external housing 2 and then passes into the area of the antechamber 13 in the internal housing 3. In this bottom area, the external housing 2 forms a part of the outer wall of the antechamber 13. The external housing 2 has a ventilation aperture 10 vertically above an inlet opening 8. A channel 7 is formed between this inlet opening 8 and the ventilation aperture 10, through which the rapidly entering foam may be directed away again immediately if necessary.

FIG. 2 represents a cross section through device 1, particularly through the damping cup 6, along line II-II in FIG. 1. The measuring tube 9, which is part of the internal housing 3, is shown in the middle. Four protruding contact areas 20 emanate from measuring tube 9 at angles of 90°. The protruding contact areas 20 are guided and seated in corresponding grooves 21 in the external housing 2.

In operation, liquid (i.e. oil) enters the external housing 2 through the inlet opening 8, and then particularly passes into the outermost ring of the antechamber 13 formed between the external housing 2 and the internal housing 3. The liquid flows in this outer ring, and then enters the inner ring of the antechamber 13 through the inlet opening 11 which is formed in the wall 22 of the internal housing 3. The liquid must then flow through at least 180° around this inner ring again before it can enter the actual measuring tube 9 through the inlet opening 12. With this path through the outer and inner rings of the antechamber 13, the liquid is largely degassed. The level of the liquid in the measuring tube 9 rises and falls in correspondence with the level outside the device 1. To enable this, a ventilation aperture 23 is provided on the top edge of the measuring tube 9, through which air can escape, and then can also escape through the ventilation aperture 10 in the external housing 2 on the opposite side. When volumes or also particularly foam enters rapidly through the inlet opening 8 in the external housing 2, such volumes may also exit immediately via a channel 7 which is formed between the internal housing 3 and the external housing 2. In such case, the foam passes through the cutout 15 recess in the top protruding edge 14 of the internal housing 3 and reaches the channel 7 formed between the internal housing 3 and the external housing 2, and then exits upwards through ventilation aperture 10 in external housing 2.

All of the features listed in the preceding description and in the claims can be combined in any permutation with the features of the independent claim. The disclosure of the invention is thus not limited to the combinations of features that have been described and claimed, but all feature combinations that are practicable within the scope of the invention are rather to be treated as having been disclosed.

The invention claimed is:

1. A device for measuring a fill level of a liquid in a container with an ultrasonic sensor which is arranged on a floor element, wherein a damping cup with a measuring tube is assigned to the ultrasonic sensor,
    wherein the damping cup has an external housing and an internal housing,
    the internal housing includes the measuring tube,
    either the internal housing has outwardly protruding contact elements that lie against an inside of the external housing, or the external housing has inwardly protruding contact elements that lie against an outside of the internal housing, and
    the external housing is provided and designed for pluggable mounting of the internal housing,
    a channel is formed between the internal housing and the external housing,
    lower end regions of the internal housing and the external housing are connected to the floor element, and
    the lower end regions of the internal housing and/or of the external housing and/or corresponding mating surfaces on the floor element are sloping.

2. The device according to claim 1, wherein the lower end region of the internal housing has an antechamber.

3. The device according to claim 2, wherein the internal housing has a protruding edge on a top edge of the antechamber, the protruding edge closes off the antechamber at the top and is provided and designed to bear on the inside of the external housing.

4. The device according to claim 1, wherein the external housing has a ventilation aperture in an upper region.

5. The device according to claim 1, wherein in a plugged state, the internal housing protrudes beyond a bottom of the external housing.

6. The device according to claim 1, wherein the lower end regions of the internal housing and the external housing are welded to the floor element.

7. The device according to claim 1, wherein the floor element is constructed as a flange.

8. The device according to claim 1, wherein the lower end regions of the external housing have a long inclined element, and the lower end regions of the internal housing have an inclined element which is shorter than the long inclined element.

9. The device according to claim 1, wherein the protruding contact elements extend over more than half a height of the damping cup.

10. The device according to claim 1, wherein when viewed in cross section, at least three protruding contact elements are provided.

11. An internal combustion engine, particularly for a motor vehicle with an oil-lubricated engine,
    wherein the oil-lubricated engine is equipped with the device according to claim 1 for measuring the fill level of the engine oil.

* * * * *